United States Patent [19]

George

[11] Patent Number: 4,898,163
[45] Date of Patent: Feb. 6, 1990

[54] TRANSTRACHEAL AIRWAY AND PLACEMENT DEVICE

[76] Inventor: Gordon P. George, 1717 N. 1030 West, Orem, Utah 84057

[21] Appl. No.: 315,538

[22] Filed: Feb. 27, 1989

[51] Int. Cl.[4] .......................................... A61M 16/00
[52] U.S. Cl. ................... 128/200.26; 606/185
[58] Field of Search ............... 128/200.26, 207.15, 128/DIG. 26, 305, 305.3, 207.14, 772, 768, 348.1; 604/104, 107, 280, 281, 282, 283

[56] References Cited

U.S. PATENT DOCUMENTS

| | | | |
|---|---|---|---|
| 2,541,402 | 2/1951 | Caine | 128/200.26 |
| 3,182,663 | 5/1965 | Abelson | 128/305.3 |
| 3,384,087 | 5/1968 | Brummelkamp | 128/305.3 |
| 3,511,243 | 5/1970 | Toy | 128/305.3 |
| 4,244,362 | 1/1981 | Anderson | 128/200.26 |
| 4,278,081 | 7/1981 | Jones | 128/207.15 |
| 4,444,185 | 4/1984 | Shugar | 128/200.26 |
| 4,471,778 | 9/1984 | Toye | 128/305.3 |
| 4,520,810 | 6/1985 | Weiss | 128/305.3 |
| 4,643,188 | 2/1987 | Weiss | 128/305.3 |
| 4,677,978 | 7/1987 | Melker | 128/207.14 |

Primary Examiner—Eugene H. Eickholt
Attorney, Agent, or Firm—K. S. Cornaby

[57] ABSTRACT

An apparatus for establishment of an airway in transtracheal intubation via the cricothyroid membrane is disclosed in which the design integrates within a single unit a curvilinear needle with cutting blade, stylet, syringe and non-metal airway cannula in an over-the-needle position. The integrated design enhances quick and accurate placement of the airway in both emergency and non-emergency applications.

9 Claims, 7 Drawing Sheets

TRANSTRACHEAL AIRWAY AND PLACEMENT DEVICE

BACKGROUND OF THE INVENTION

This invention relates to the medical treatment of patients who have an obstructed airway by means of tracheostomy or cricothyrotomy. Under emergency circumstances, all physicians and other medical personnel, no matter what their specialty, are expected to know how to protect and maintain a patient's airway. Even under non-emergency circumstances, an anesthesiologist, for example, must maintain the airway, ventilation, and oxygenation of a patient who has been rendered unconscious by the doctor or another health care professional by use of sedatives, hypnotics, or other agents. These responsibilities have extended even to such health care professionals as dentists, podiatrists, and emergency medical technicians- persons who may witness an allergic reaction in a patient brought on by use of drugs or remedies which have been administered.

The typical methods of maintaining a patient's airway are by anatomical positioning, clearing the passageway of foreign materials, positive pressure mask ventilation, oral/nasal airways, or oral/nasal approach to tracheal intubation. Following failure of all of the typical methods of ventilation, the last method of resort is transtracheal intubation via formal tracheostomy or cricothyrotomy. These procedures, though infrequently required, are recommended for use as a last means method. See, *Clinics of Anesthesiology*, Tunstall and Sheikh, 1986.

In many patients, establishment of the airway may be formidable due to morphological anomalies, such as a large tongue, excessive soft tissue or tracheal displacement. Inabilities of the patient to extend the head and neck or to open the mouth wide enough contribute to the difficulty of maintaining the airway, as do other morphological anomalies or physiological events such as floppy epiglottis or laryngospasm.

Even the use of formal tracheostomy presents inherent problems. Tracheostomy requires instrumentation which may not be available in emergency situations. Additionally, given the time constraints involved in an emergency, a tracheostomy may yield to the more expedient procedure of cricothyrotomy. Circothyrotomy, considered by many to be the preferred method of establishing an airway after other methods have failed, is achieved by transtracheal intubation via a percutaneous puncture through the cricothyroid membrane into the trachea.

Methods for performing transtracheal intubation have been disclosed in the prior art. U.S. Pat. No. 4,677,978 to Melker describes a method for establishing a transtracheal airway. However, by its design, the method is inherently ineffective in that once the percutaneous placement of the needle is made, the needle and syringe are removed so that a guide wire can be placed through the catheter; this feature of the method significantly increases the risk that the tube has not been properly placed in the trachea, and subsequent placement of the wire through the catheter may result in the wire being threaded into the subcutaneous tissues, or be unable to be threaded at all. The system is also of a design which requires the user to look away momentarily to grasp other pieces of the instrument, movement which greatly impedes the quick and accurate placement of the device.

Other devices exist on the market which have drawbacks similar to those described above. In particular, these devices are complex, difficult to use and manipulate and often requiring instructions. It requires the practitioner to look away during placement of the device which greatly increases the chance of improper establishment of the airway. Even devices on the market which are composed of a simple curved metal needle with attached blade and syringe present problems in placement. In use, the hollow needle of the device may be properly placed, but the tip of the blade may be improperly positioned in the back wall of the trachea. Also, if the patient moves, coughs, or begins to choke in a gagging response, the blade may act as a scalpel causing severe damage.

The invention herein presents a new and more easily utilized apparatus for achieving cricothyrotomy which overcomes many of the problems encountered with the other methods enumerated above. Ideally, a transtracheal device should be designed for rapid and easy placement, with a high rate of success in establishing and maintaining the patient's airway, while being safe to use, easily utilized by all practitioners regardless of level of expertise, and should be concentrically and concisely designed. The invention herein fulfills these objectives, and therefore presents a new and useful device in relation to the prior art.

SUMMARY OF THE INVENTION

The present invention is designed to facilitate transtracheal intubation via percutaneous puncture through the cricothyroid membrane. It comprises a curvilinear hollow metal needle with a sharp blade-like surface at the distal end for penetration of the cricothyroid membrane, a hollow-barreled syringe means, and a plunger, slideably disposed within the syringe, to the distal end of which is attached a flexible stylet. The curved needle is inserted through the membrane. The placement of the blade in this design allows the practitioner to hold the device in close proximity to the patient, enabling the user to exercise fine control of the needle. The curvature of the needle allows the syringe component to be free of possible disturbance by movement of the patient's chin. Once placed, the plunger of the syringe is retracted to aspirate a small amount of air. Assured that the needle placement is correct, the plunger is then advanced through the syringe simultaneously advancing the stylet out of the needle into the trachea. Thereafter, a final airway catheter which is in an over-the-needle position is threaded down the needle and subsequently over the stylet into the trachea. The needle and stylet are then removed leaving the airway in place. The airway has a threaded means at the proximal end to which airway modification devices or tubes may be attached, and is tapered at its distal end to facilitate unencumbered insertion. The final airway catheter may be composed of rigid, semi-rigid or flexible plastic or other synthetic material which has a sufficient quality of rigidity to prevent kinking. The airway may also be composed of a "memory" material which will cause it to assume a predetermined shape when not being manipulated in relation to the stylet or needle.

In a modification to the preferred embodiment, the stylet is not attached to the distal end of the plunger. In this embodiment, the stylet is comprised of a hollow tube through which air may be aspirated both before and after the stylet has been advanced into the trachea. All other aspects of airway placement and withdrawal of the integrated device are as described for the preferred embodiment.

In another embodiment of this device, the syringe is a "double-barrelled" design tapering at the distal end to form one common chamber to which the metal needle attaches. Slideably disposed within one barrel is the plunger, and the other barrel maintains the stylet. When retracted, the plunger causes air to be aspirated through the metal needle via the common chamber. A gasket at the proximal end of the stylet barrel prohibits air from being spirated from the outside. The stylet is actuated by a lever, attached to the proximal end of the stylet, which passes through and is slideable disposed along the length of the barrel of the syringe housing the stylet. When the lever is manually pulled toward the proximal end of the device, the stylet moves through the metal needle; when the lever is advanced down the stylet barrel of the syringe, the stylet simultaneously advances through the needle and protrudes out the distal end of the needle.

With any of these embodiments, a dilator may be placed over the needle followed by the non-metal airway over the dilator. The dilator apparatus allows the use of a smaller needle and stylet, and allows for the use of a larger final airway. The dilator has a tapered distal end which reduces resistance to advancement of the apparatus into the trachea. Further, with any of the embodiments described, a metal needle may be used which has a hollow conduit integrally manufactured into the inside wall of the needle. The conduit runs the length of the needle and allows for the use of a stylet which is of substantially the same diameter as the inner diameter of the needle. The conduit in the needle thus provides a means for aspirating air from the trachea when the plunger is retracted. Alternatively, a stylet may be used which is hollow and which allows aspirated air to pass through into the syringe.

This new apparatus may be used in either emergency situations or as an elective means of establishing an airway. Though the embodiment disclosed is optimally used in high flow (jet) oxygenation and/or anesthesia, the airway established by the apparatus has the ability to be used in low flow oxygenation and/or anesthesia either by continuous or discontinuous positive pressure changes. Indeed, many experts in the field have shown that transtracheal oxygenation at greater than four liters per minute flow, via an 18 gauge needle or catheter, can sustain acceptably normal oxygenation in anesthetized patients who have otherwise obstructed airways. Further, it has been shown that constant low pressure flow, constant "machine" pressure limit flow, or high flow "jet" ventilation through a percutaneous 14 gauge needle catheter can satisfactorily accomplish oxygenation of the patient.

The present invention meets the optimal requirements desired in a transtracheal intubation device because the integral design allows accurate and quick placement of the device without having to reach for other parts. The combination of the IV needle and the syringe-type design, familiar to all health care practitioners, makes the device easy to understand and use. These and other advantages of the present invention will become apparent in the following discussion.

DETAILED DESCRIPTION OF THE PREFERRED EMBODIMENTS

Figure 1:
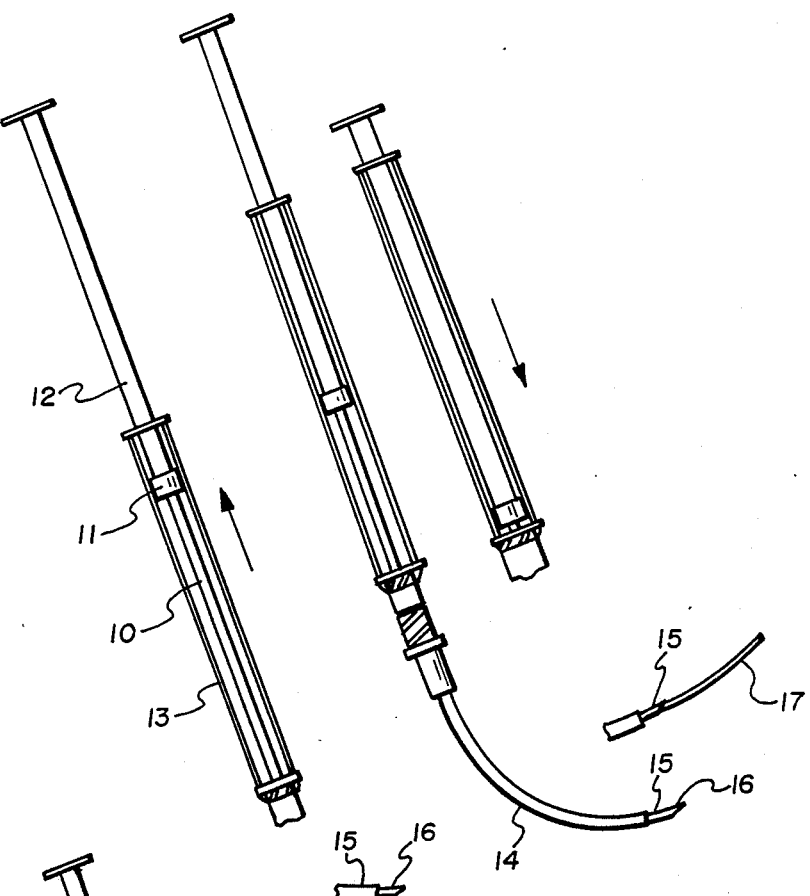
FIG. 1 is a partially cross-sectioned view of the embodiment where the plunger and stylet are attached.

The single-barrel embodiment of the device is illustrated in FIG. 1 in which the stylet 10 is attached to the bottom surface 11 of the plunger 12, which is slideably disposed within the syringe 13. When the plunger is being pulled to the fully retracted position so as to cause aspiration of air from the trachea, the stylet is completely retracted within the needle and air is allowed to pass around the stylet and into the barrel of the syringe. When the plunger is at a position half way through the syringe, the device is said to be loaded. As illustrated by the "loaded position" in the center of FIG. 1, the final airway 14 is in the over-the-needle position (the curvilinear needle being disposed inside the airway), and the tip of the needle 15 with the blade 16 is extended beyond the end of the airway. As shown, the needle is preferably curved, but the needle may be of varying curvature, or it may be straight. As the plunger is advanced forward, the stylet is propelled through the needle 15, and the distal end of the stylet 17 extends out from the end of the needle, into the trachea.

Figure 2:
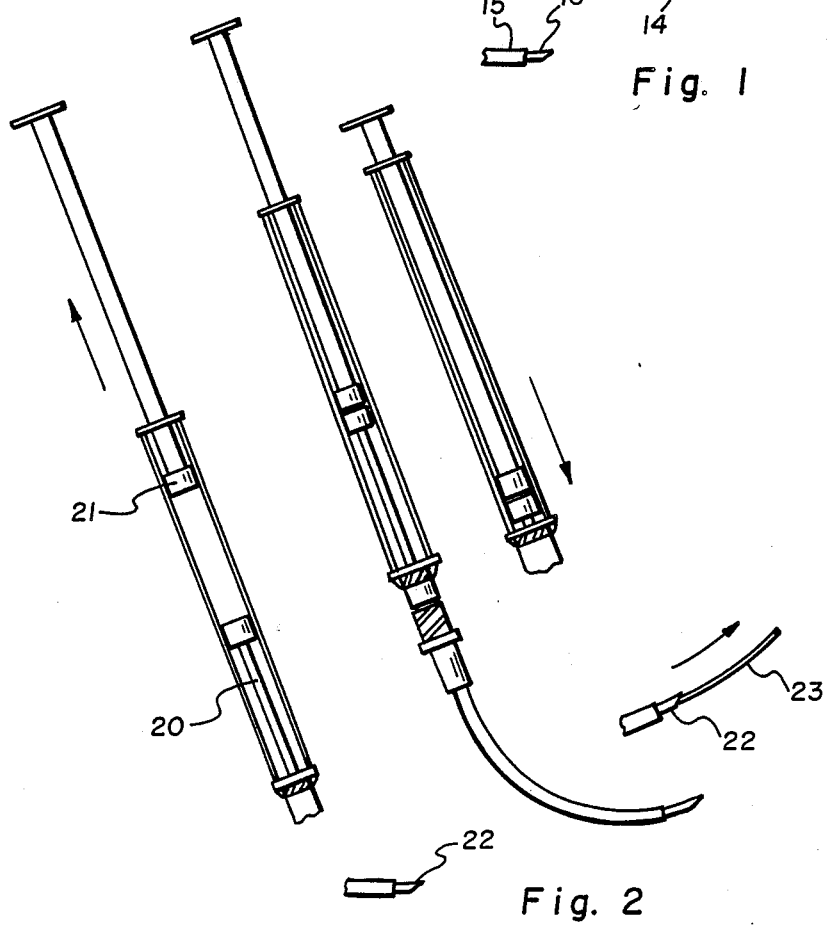
FIG. 2 is a partially cross-sectioned view of the embodiment where the plunger and stylet are separate from one another.

In FIG. 2 an alternative embodiment is illustrated in which the stylet 20 is not attached to the plunger 21, and the stylet, therefore, does not move when the plunger is retracted for aspiration of air. It should be noted that the stylet is withdrawn into the needle. In this position air is allowed through the stylet and into the syringe by withdrawal of the plunger. As the plunger is advanced past the "loaded position", the stylet is propelled through the needle 22 and the distal end of the stylet 23 extends past the needle into the trachea.

Figure 3:
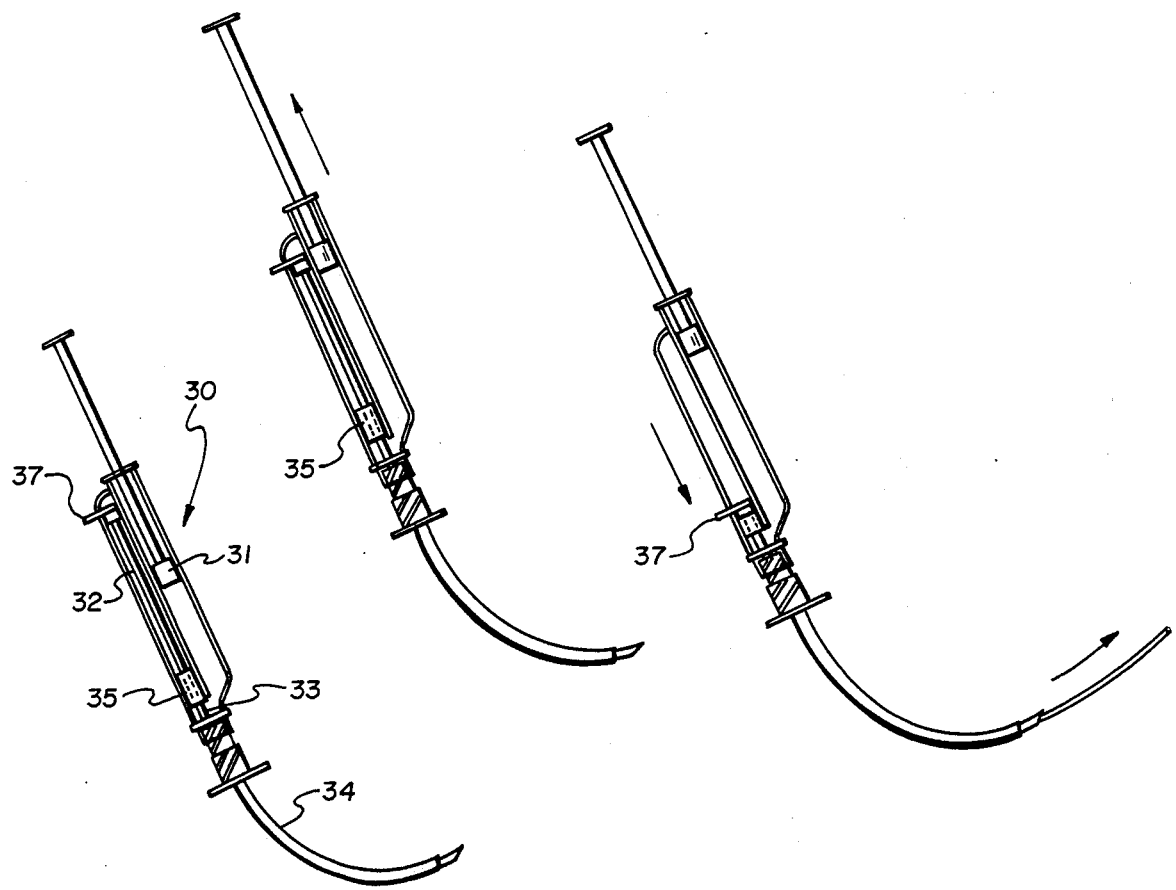
FIG. 3 is a partially cross-sectioned view of the double-barrelled syringe embodiment.

FIG. 3 illustrates the double-barrel embodiment of the syringe, generally at 30. The plunger 31 is slideably disposed within one barrel of the syringe, and the stylet 32 is slideably disposed within the other barrel of the syringe. The distal end of the syringe narrows to become a single opening 33 to which is attached the needle (disposed within the airway) and airway 34. As the plunger is retracted, aspirated air passes up through the metal needle and in through the opening of the syringe 33. A gasket 35 at the distal end of the stylet barrel slideably disposed about the stylet disallows any aspiration of air from the stylet barrel. The stylet is actuated by a lever 37 attached to the proximal end of the stylet and extends through the wall of the stylet barrel, moving up and down the length of the barrel through a slit therein. Again, as the stylet is advanced forward by movement of the lever 37 in a downward fashion, the stylet advances through the needle and out into the trachea.

Figure 4:
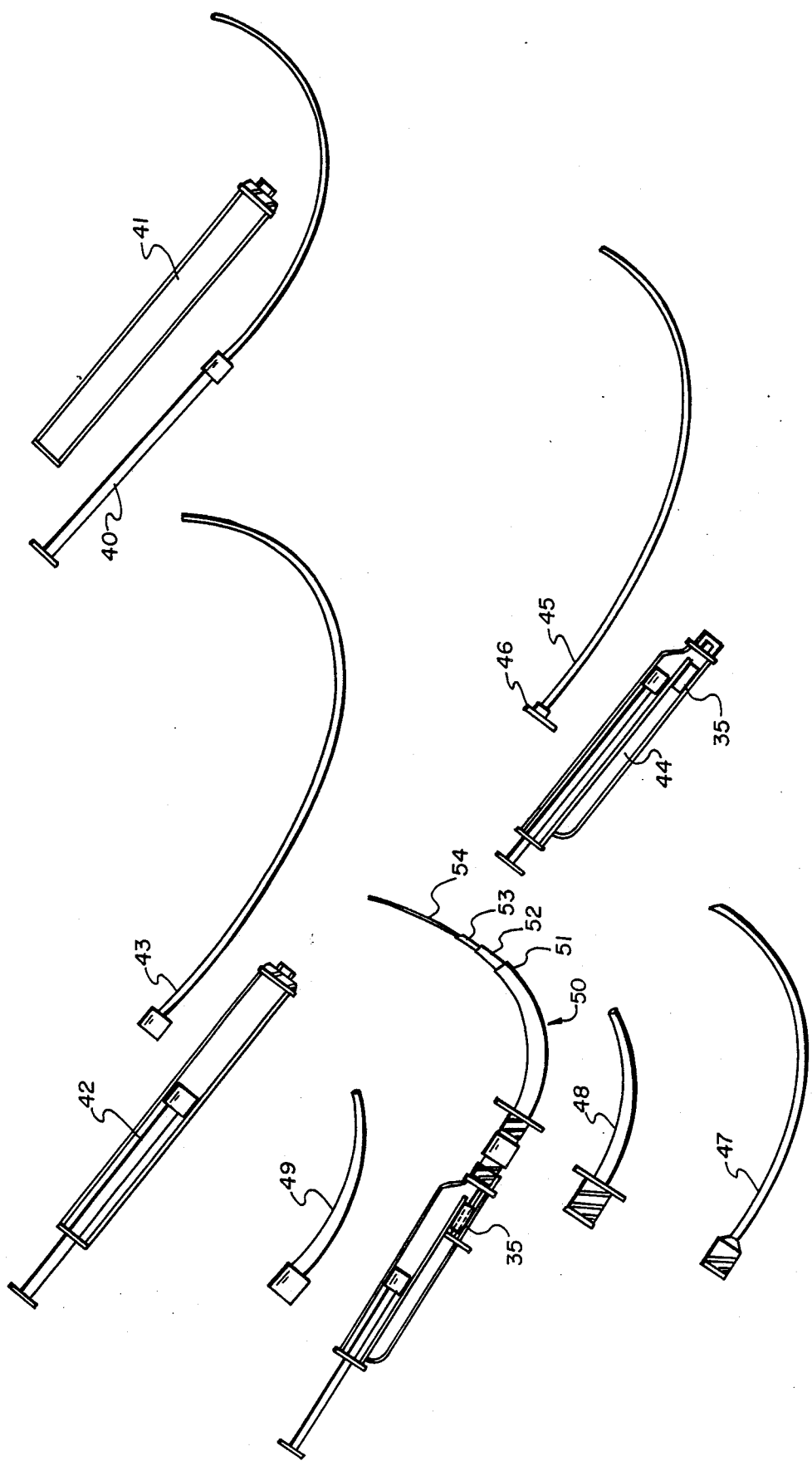
FIG. 4 is a display of the separate components of all the embodiments.

FIG. 4 illustrates the component parts of the various embodiments. The plunger with attached stylet 40 is shown separated from the single barrel syringe 41. The separated plunger 42 and hollow stylet 43 are also illustrated. The double-barrel syringe with plunger 44 is illustrated beside the stylet 45 with actuating lever 46. The metal curvilinear needle 47 with blade at the distal end is illustrated, as are the final airway 48 and dilator 49. The integrated configuration of each of these component parts is illustrated at 50 in which the airway 51 is slideably disposed upon the dilator 52 which is slideably disposed upon the needle 53 through which the stylet 54 extends. It should be noted that the ultimate size of the invention, in any embodiment, may vary to accommodate use in any size patient, from child to adult.

Figure 5:
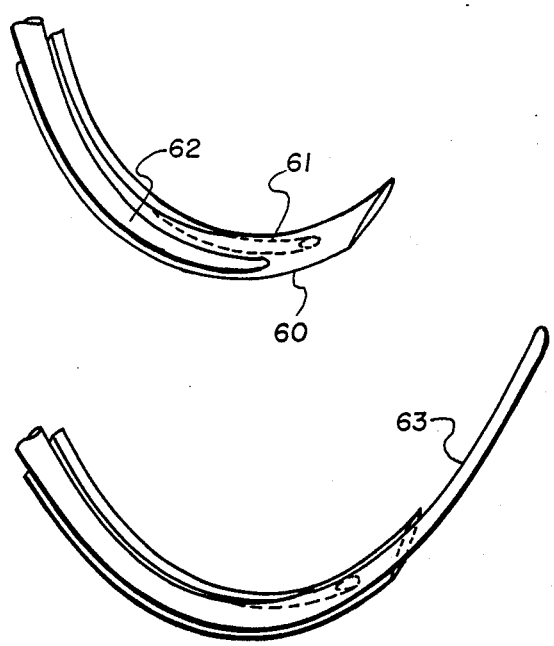
FIG. 5 is an enlarged cross-section of the modified metal needle illustrating the internal conduit.

FIG. 5 is a cross-section view of the modified metal needle 60 into one wall of which has been manufactured a hollow conduit 61. When the stylet 62 is in the retracted position, aspirated air enters the end of the needle and is carried through the conduit into the syringe (not shown). When the stylet 63 is propelled forward through the metal needle and into the trachea, the conduit is blocked.

Figure 6:
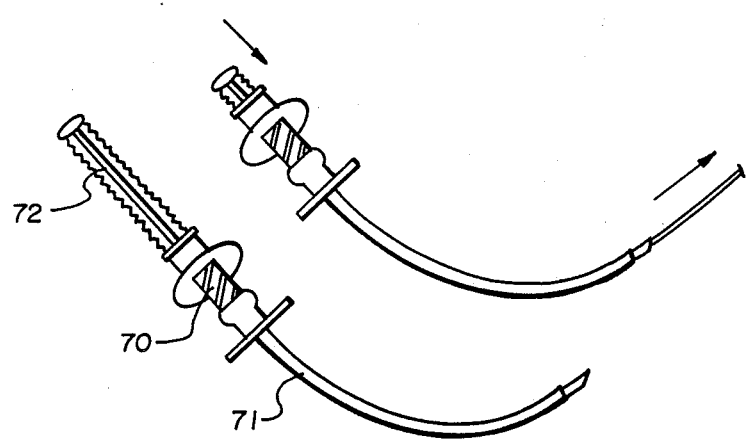
FIG. 6 is a further embodiment of the device in which the needle, stylet, and airway are without attachment to a syringe.

A further embodiment of the device is illustrated in FIG. 6 in which the needle 70 and overlying airway 71 are not attached to a syringe. The stylet 72 is manually advanced through the needle and into the trachea. In this embodiment, aspiration of air is impossible, but the other principles relating to the placement of the device without a syringe are as stated above for other embodiments.

Figure 7:
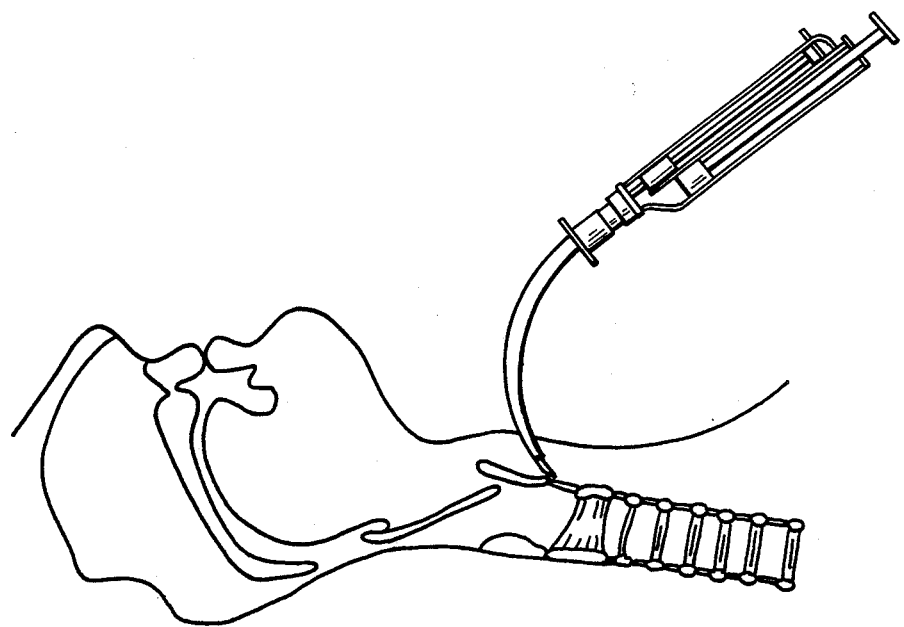
FIG. 7 is a partially cross-sectioned view of the device illustrating placement through the cricothyroid membrane.
Figure 8:
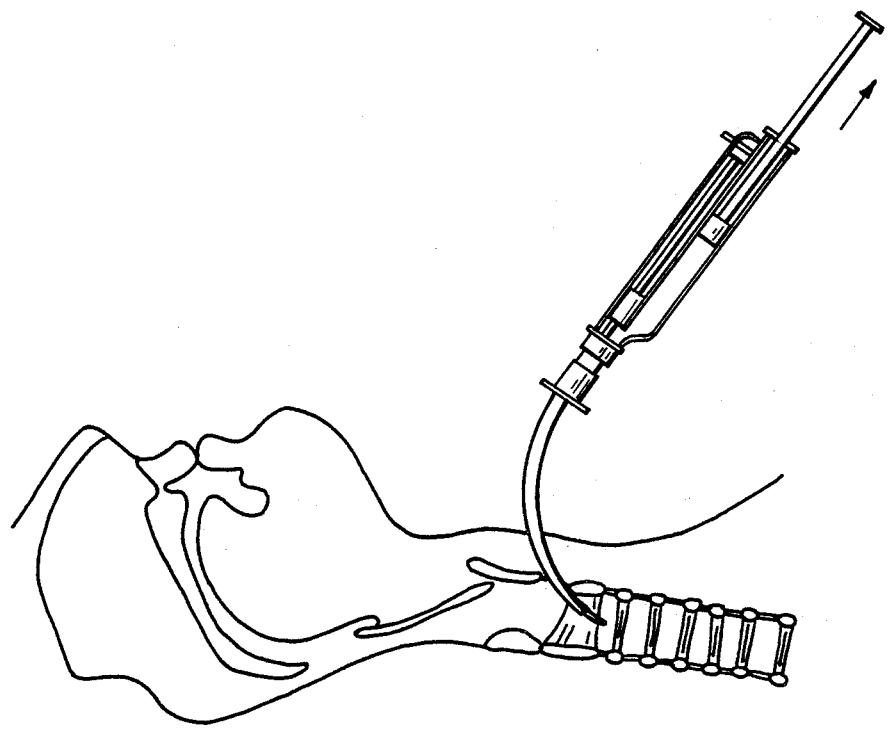
FIG. 8 is a partially cross-sectioned view of the device illustrating advanced placement of the device in the trachea.
Figure 9:
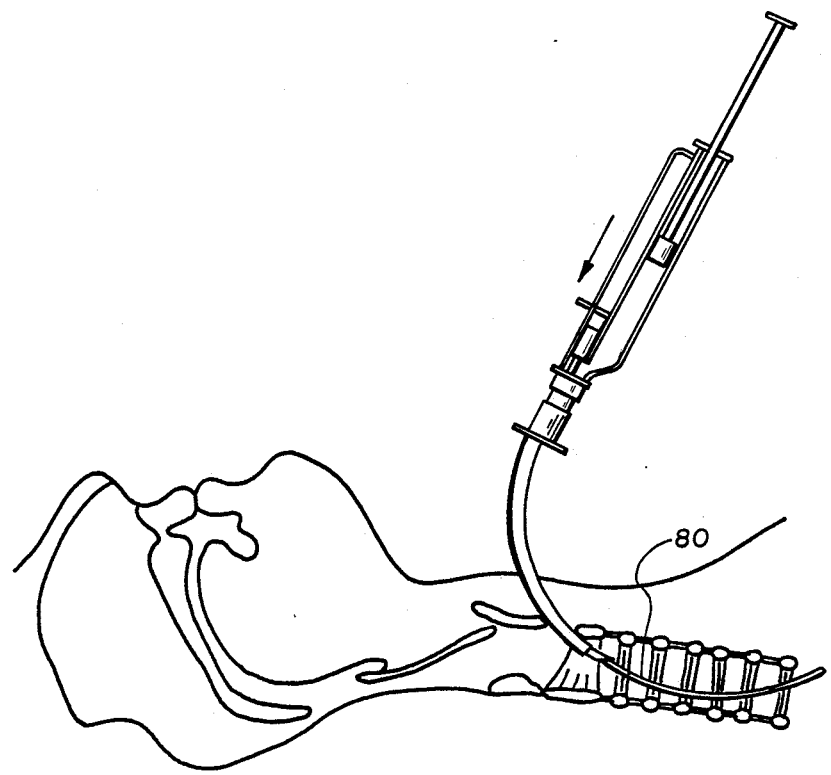
FIG. 9 is a partially cross-sectioned view of the device illustrating advancement of the stylet through the needle.
Figure 10:
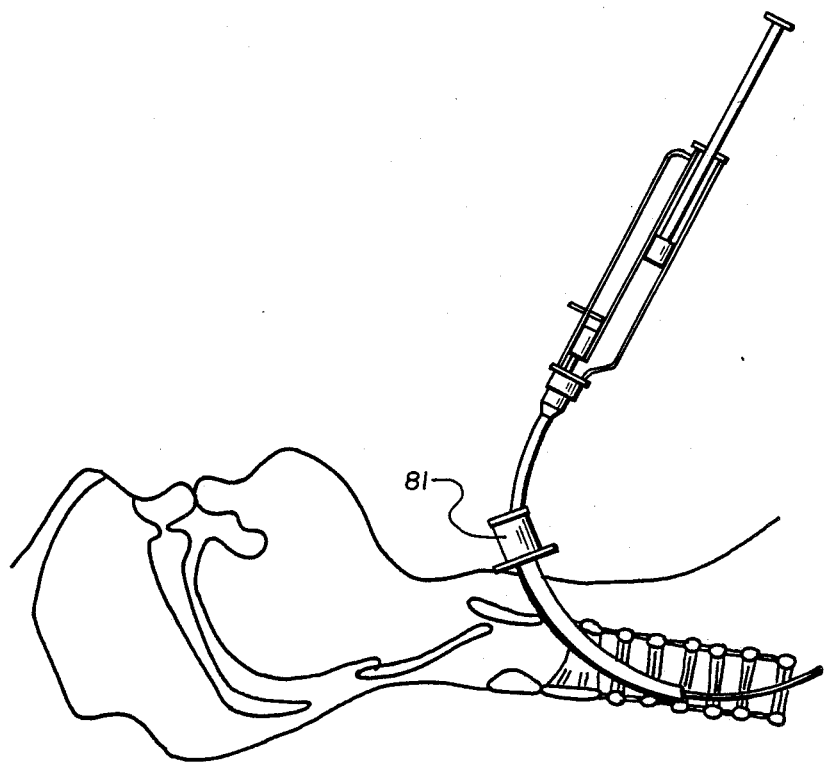
FIG. 10 is a partially cross-sectioned view of the device illustrating placement of the airway.
Figure 11:
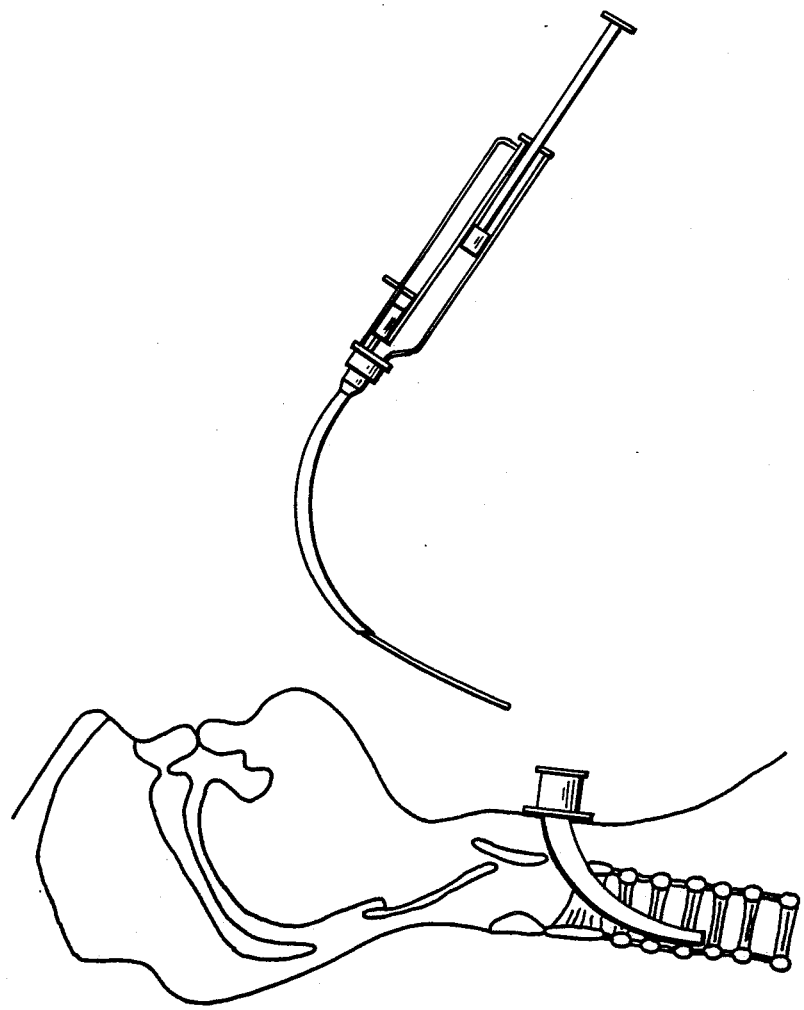
FIG. 11 is a partially cross-sectioned view of the device illustrating removal of the needle, stylet, and syringe, leaving the airway in place.

Placement of the device during a transtracheal intubation episode is illustrated in FIGS. 7 through 11 using the double-barrel embodiment of the invention. In FIG. 7 the needle has been inserted into the neck of the patient and the blade of the needle is poised over the cricothyroid membrane ready for insertion into the trachea. In FIG. 8 the needle is advanced into the trachea, and the plunger of the device is retracted for aspiration of air to assure correct placement. In FIG. 9, the stylet is advanced, as indicated by the arrow direction, and the stylet 80 is shown extended past the needle into the trachea. The airway 81 is advanced into the trachea guided by the stylet as illustrated in FIG. 10. Finally, the integral device, including stylet, needle and syringe means, is removed from the patient leaving the airway in place within the trachea.

It is understood that the particular process of the invention described herein is preferred. Obviously, numerous additional modifications and variations of the present process are possible in light of the above teachings such as intravenous use, intraplural or intraabdominal or urological use. It is therefore to be understood that within the scope of the appended claims, the process may be practiced otherwise than as specifically described herein.

I claim:

1. An apparatus for performing transtracheal intubation via the cricothyroid membrane comprising, in combination:
    a syringe means comprising at least one hollow barrel with a distal end adapted for attachment of integral apparatus means;
    a plunger means slideably disposed within said hollow barrel of said syringe means;
    a flexible stylet means slideably disposed within said barrel of said syringe means;
    a hollow curvilinear needle means integrally attached to said distal end of said syringe means, said needle means having at its distal end a sharpened edge to serve as a cutting blade; and
    a non-metal hollow tube airway means which is slideably disposed over said needle means.

2. An apparatus as set forth in claim 1 in which said syringe means is comprised of a double-barrel means in which said plunger means is slideably disposed within one barrel, and said stylet means is slideably disposed within the other barrel.

3. An apparatus as set forth in claim 1 in which said stylet means is integrally attached to said plunger means.

4. An apparatus as set forth in claim 1 which further comprises a hollow tube means for dilation of the trachea which is slideably disposed over said hollow tube airway means.

5. An apparatus as set forth in claim 1 in which said stylet means is hollow.

6. An apparatus as set forth in claim 1 in which said needle means further comprises a hollowed conduit along the entire length of said needle means.

7. An apparatus as set forth in claim 1 in which said needle means is straight.

8. An apparatus as set forth in claim 1 in which said hollow tube airway means may be manufactured of a material which retains a preformed shape original to its manufacture once placed within the body cavity.

9. An apparatus as set forth in claim 1 in which said hollow tube airway means is curvilinear and of a semi-rigid material.

* * * * *